United States Patent
Kelly

(10) Patent No.: US 10,350,436 B2
(45) Date of Patent: Jul. 16, 2019

(54) RADIOSURGICAL PLANNING AND TREATMENT

(71) Applicant: Rising Tide Foundation, Schaufhaussen (CH)

(72) Inventor: Douglas A. Kelly, Tulsa, OK (US)

(73) Assignee: INTERNATIONAL PRIVATE BANK LLC, St. Thomas, VI (US)

(*) Notice: Subject to any disclaimer, the term of this patent is extended or adjusted under 35 U.S.C. 154(b) by 0 days.

(21) Appl. No.: 15/813,036

(22) Filed: Nov. 14, 2017

(65) Prior Publication Data

US 2018/0078788 A1     Mar. 22, 2018

Related U.S. Application Data

(62) Division of application No. 14/334,685, filed on Jul. 18, 2014, now Pat. No. 9,956,428.

(51) Int. Cl.
   *A61N 5/10*  (2006.01)

(52) U.S. Cl.
   CPC ........... *A61N 5/1039* (2013.01); *A61N 5/103* (2013.01); *A61N 5/1083* (2013.01); *A61N 5/1084* (2013.01)

(58) Field of Classification Search
   CPC .... A61N 5/103; A61N 5/1031; A61N 5/1039; A61N 5/1037
   USPC .................................................. 600/1; 378/65
   See application file for complete search history.

(56) References Cited

U.S. PATENT DOCUMENTS 6,477,229 B1 * 11/2002 Grosser ................ A61N 5/1031
                                                           378/65
8,613,694 B2 * 12/2013 Walsh ..................... A61N 5/103
                                                           378/65

FOREIGN PATENT DOCUMENTS

| EP | 1793895 A2 | 6/2007 |
| EP | 2260902 A1 | 12/2010 |
| EP | 2349480 A1 | 8/2011 |
| WO | WO-2003092789 A2 | 11/2003 |
| WO | WO-2008115830 A2 | 9/2008 |

OTHER PUBLICATIONS

Kim et al., "Single-Dose Versus Fractionated Stereotactic Radiotherapy for Brain Metastases," International Journal of Radiation: Oncology Biology Physics, Pergamon Press, USA, May 10, 2010, vol. 81, No. 2, XP028279740, ISSN: 0360-3016, pp. 483-489.

T. Murai et al., "Fractionated Stereotactic Radiotherapy using CyberKnife for the Treatment of Large Brain Metastases: A Dose Escalation Study," Clinical Oncology, Mar. 1, 2014, vol. 26, No. 3, ISSN: 0936-6555, Amsterdam, NL., p. 151-158.

(Continued)

*Primary Examiner* — Samuel G Gilbert
(74) *Attorney, Agent, or Firm* — McDermott Will & Emery LLP

(57) ABSTRACT

Multiple tumors are grouped into multiple treatment groups. Tumors in different treatment groups are treated by a radiosurgery in different treatment sessions than the tumors in the same treatment groups. The tumors can be grouped so as to decrease the biologically effective dose received by normal tissue in the treatment area. The radiosurgical planning system can divide the tumors into groups based on their location relative to each other and the radiation the tumors will be treated with and create a plan for treating the tumors according to the treatment groups.

16 Claims, 9 Drawing Sheets

(56) References Cited

OTHER PUBLICATIONS

Unkelbach et al., "Simultaneous optimization of dose distributions and fractionation schemes in particle radiotherapy," Med. Phys., vol. 40, Section 9, Sep. 2013, pp. 091702-1-091702-11.

Unkelbach et al., "Spatiotemporal fractionation schemes for liver stereotactic body radiotherapy," Radiotherapy and Oncology, vol. 125, Sep. 23, 2017, pp. 357-364.

Unkelbach et al., "The dependence of optimal fractionation schemes on the spatial dose distribution," Institute of Physics and Engineering in Medicine, Physics in Medicine and Biology, vol. 58, Dec. 10, 2012, pp. 159-167.

Wegner et al., "Fractionated Stereotactic Radiosurgery for Large Brain Metastases," American Journal of Clinical Oncology (Cancer Clinical Trials), 2013, vol. 38, No. 2, XP055230093, US ISSN: 0277-3732, Pittsburgh, PA., pp. 135-139.

* cited by examiner

PTV Report

| PTV ID | Centroid | Volume |
|---|---|---|
| PTV 1 | $(X_1, Y_1, Z_1)$ | $V_1$ |
| PTV 2 | $(X_2, Y_2, Z_2)$ | $V_2$ |
| PTV 3 | $(X_3, Y_3, Z_3)$ | $V_3$ |
| PTV 4 | $(X_4, Y_4, Z_4)$ | $V_4$ |
| PTV 5 | $(X_5, Y_5, Z_5)$ | $V_5$ |

FIG. 7

- Determine Quantity of Tumors
- Determine Quantity of Treatment Groups
- Assign Tumors to Treatment Groups

FIG. 8

RADIOSURGICAL PLANNING AND TREATMENT

RELATED APPLICATIONS

This application is a divisional of U.S. patent application Ser. No. 14/334,685, filed on Jul. 18, 2014, which is incorporated herein by reference.

BACKGROUND

Radiosurgery has become increasing popular in recent years. The aim of radiosurgery is for a large dose of radiation to be targeted to an affected area, while the damage to surrounding normal tissue is kept to a minimum. This is can be very useful in treatment areas where the surrounding tissue performs a critical function, for example the brain and lungs.

Radiosurgery was originally developed to treat brain tumors, but has since been expanded to treat many other target organs, including: breast, lung, prostate, liver, spine, kidney, adrenal, pancreatic, bone, abdominal and soft-tissues. As the utility of radiosurgical methods increase, the need to address the concerns with the procedure become even more pressing as more patients will be undergoing the treatment.

To treat a single tumor with radiosurgery dozens or hundreds of radiation beams are targeted to enter the body from different angles. Each beam intersects the tumor and the region where all the beams intersect results in a summation of the radiation of each individual beam and the tumor receives the full dose. However, the beams must each pass through normal tissue to reach the intended target and therefore those normal tissues also receive a partial radiation dose. Since it is such a small dose that passes through with any single beam, the radiation does not result in much damage to the normal tissues and is usually tolerable to the patient.

Brain metastases are a common clinical problem in cancer patients. They occur in 20-40% of all cancer diagnoses, especially in lung, breast, kidney and melanoma cancer patients. As these numbers continue to increase, there will be more and more patients undergoing radiosurgery for the treatment of their tumors.

SUMMARY

In general terms, this disclosure is directed to radiosurgical treatment of tumors. In one possible configuration and by non-limiting example, multiple tumors are treated using radiosurgery, such as by assigning the tumors to different treatment groups, and treating the tumors in each group on different days.

One aspect is a method of treating multiple tumors using radiosurgery, the method comprising: assigning each of the tumors to one of a plurality of treatment groups, wherein a quantity of treatment groups is less than a quantity of the tumors; and irradiating the tumors using a radiosurgery device in multiple treatment sessions based on the assigned treatment groups, wherein tumors assigned to different treatment groups are treated during different treatment sessions.

Another aspect is a method of generating a treatment schedule for radiosurgery, the method comprising: assigning each of the tumors to one of a plurality of treatment groups using a computing device, wherein a quantity of treatment groups is less than a quantity of the tumors; and generating a treatment schedule including multiple treatment sessions using the computing device, wherein the tumors assigned to different treatment groups are treated in different treatment sessions.

A further aspect is a radiosurgery treatment planning system comprising: at least one processing device; and at least one computer readable storage device, the at least one computer readable storage device storing data instructions that when executed by the at least one processing device cause the at least one processing device to: assign each of multiple tumors to one of a plurality of treatment groups, wherein a quantity of treatment groups is less than a quantity of tumors; and generate a treatment schedule including multiple treatment sessions, wherein tumors assigned to different treatment groups are treated in different treatment sessions.

BRIEF DESCRIPTION OF THE DRAWINGS

FIG. 7 is a schematic block diagram illustrating an example PTV report generated by a planning target volume definition engine.

FIG. 8 is a flow chart illustrating an example method of grouping tumors.

DETAILED DESCRIPTION

Figure 1:
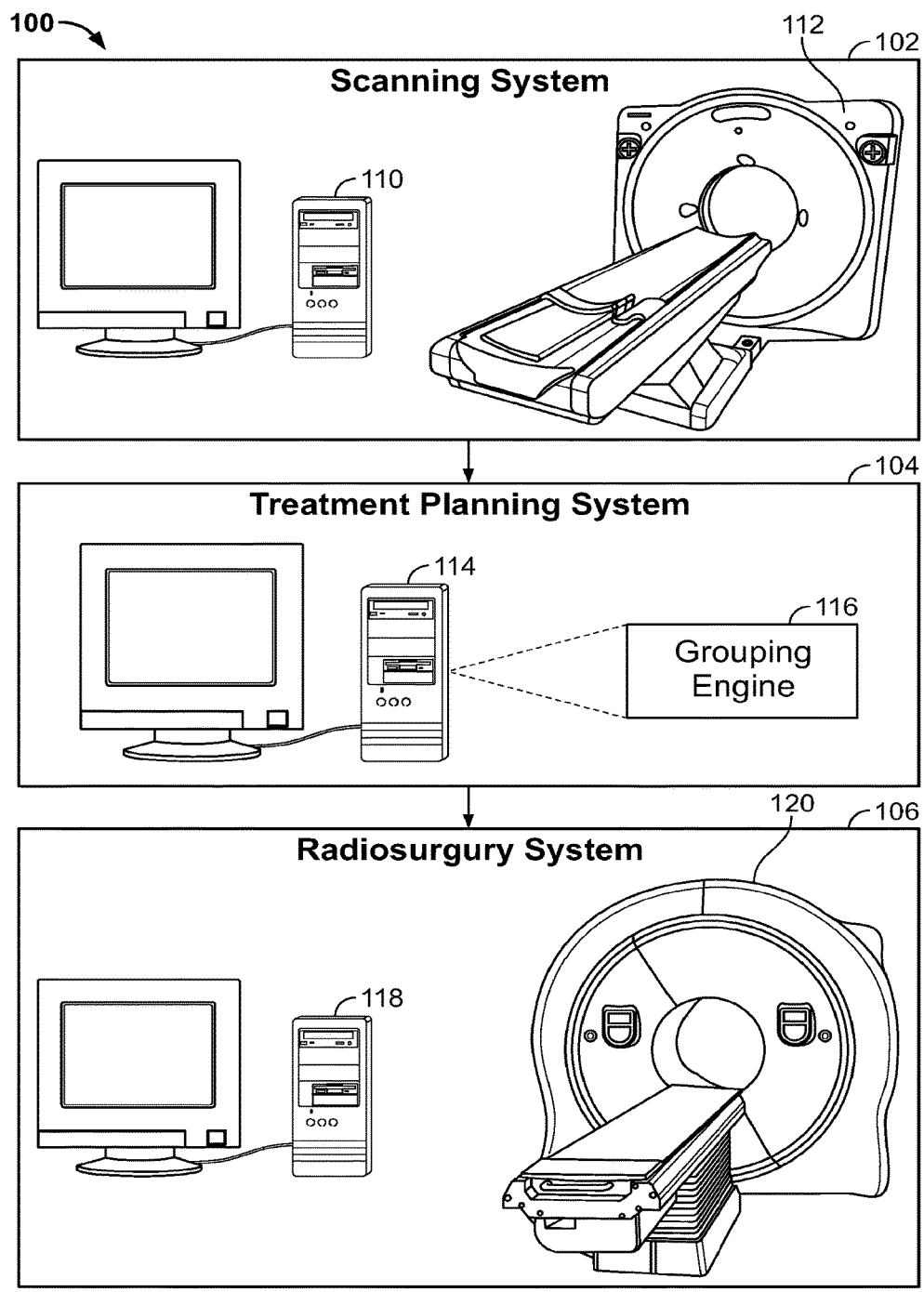
FIG. 1 is a schematic block diagram illustrating an example of a planning and treatment system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic block diagram illustrating an example of a planning and treatment system 100. In this example, the planning and treatment system 100 includes a scanning system 102, a treatment planning system 104, and a radiosurgery system 106. In this example, the scanning system 102 includes a computing device 110 and a scanning device 112. The example treatment planning system 114 includes a computing device 114 including a grouping engine 116. The example radiosurgery system 106 includes a computing device 118 and a radiosurgery device 120.

The scanning system 102 includes the scanning device 112 that operates to scan an area of interest within a patient's body. An example of the scanning device 112 is an x-ray computed tomography (CT) scanning device. The scanning system 102 generates images of the area of interest, which allows for the identification of normal tissue and abnormal tissue, such as tumors. An example of the scanning system 102 is illustrated and described in more detail with reference to FIG. 2.

The treatment planning system 104 operates to generate a treatment plan for the patient. In some embodiments the treatment plan uses the images generated by the scanning system 102, for example. In some embodiments the treatment planning system 104 includes a computing device 114 and a grouping engine 116. An example of the treatment planning system 104 is illustrated and described in more detail with reference to FIGS. 4-11.

The radiosurgery system 106 operates to provide radiation therapy to the patient according to the treatment plan. In some embodiments the radiosurgery system 106 includes a computing device 118 and a radiosurgery device 120. Examples of the radiosurgery system 106 are illustrated and described in more detail with reference to FIG. 12.

Figure 2:
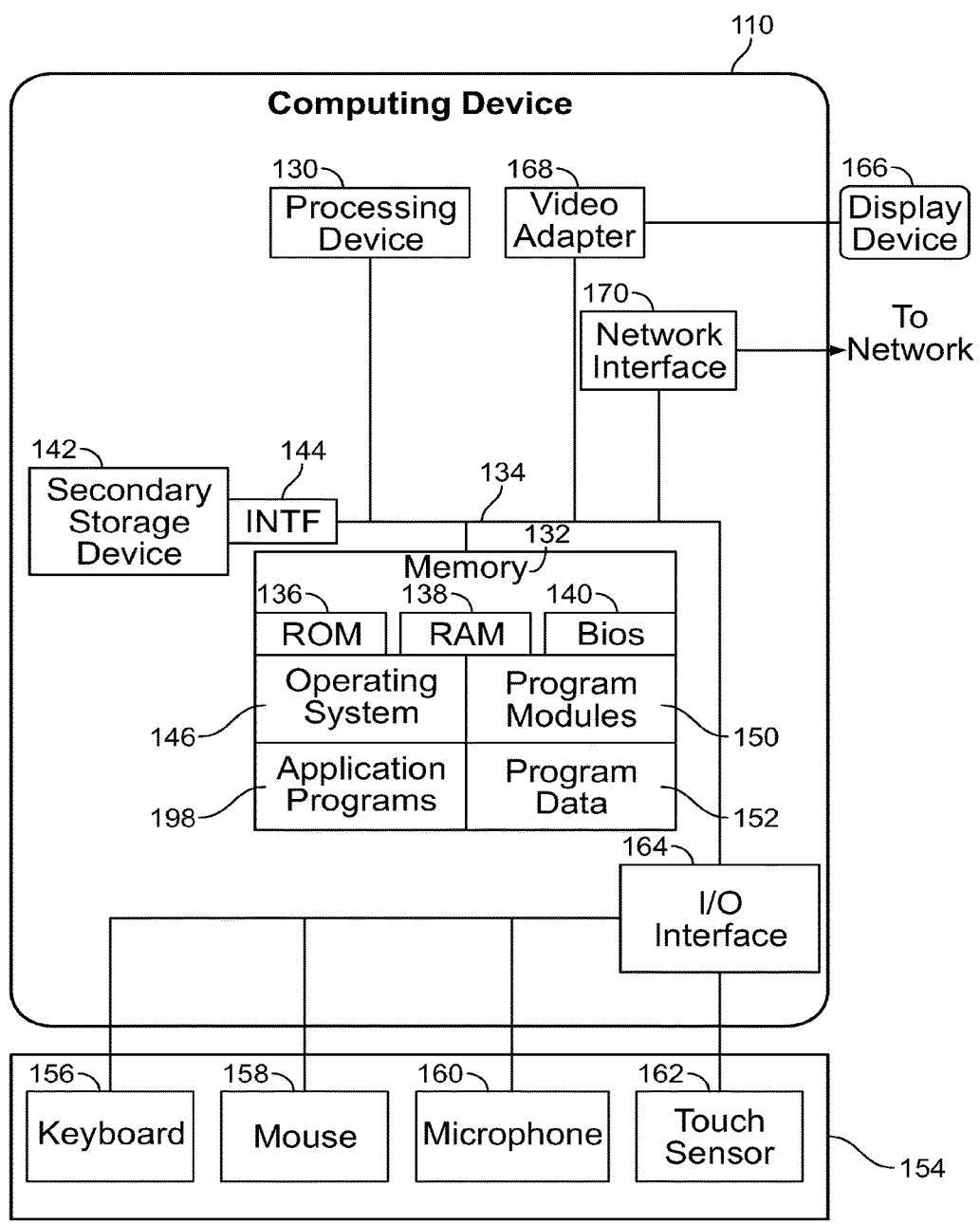
FIG. 2 illustrates an exemplary architecture of a computing device that can be used to implement aspects of the present disclosure.

FIG. 2 illustrates an exemplary architecture of a computing device that can be used to implement aspects of the present disclosure, including any of the plurality of computing devices discussed herein. The computing device illustrated in FIG. 2 can be used to execute the operating system, application programs, and software modules (including the software engines) described herein. By way of example, the computing device is described below as the computing device 110 of the scanning system 102. To avoid undue repetition, this description of the computing device will not be separately repeated herein for each of the other computing devices, including the computing device 114 of the treatment planning system 104, the computing device 118 of the radiosurgery system 106, or any other computing device that may be part of the planning and treatment system 100, but such devices can also be configured as illustrated and described with reference to FIG. 2.

The computing device 110 includes, in some embodiments, at least one processing device 130, such as a central processing unit (CPU). A variety of processing devices are available from a variety of manufacturers, for example, Intel or Advanced Micro Devices. In this example, the computing device 110 also includes a system memory 132, and a system bus 134 that couples various system components including the system memory 132 to the processing device 130. The system bus 134 is one of any number of types of bus structures including a memory bus, or memory controller; a peripheral bus; and a local bus using any of a variety of bus architectures.

Examples of computing devices suitable for the computing device 110 include a server computer, a desktop computer, a laptop computer, a tablet computer, a mobile computing device (such as a smart phone, an iPod® or iPad® mobile digital device, or other mobile devices), or other devices configured to process digital instructions.

The system memory 132 includes read only memory 136 and random access memory 138. A basic input/output system 140 containing the basic routines that act to transfer information within computing device 110, such as during start up, is typically stored in the read only memory 136.

The computing device 110 also includes a secondary storage device 142 in some embodiments, such as a hard disk drive, for storing digital data. The secondary storage device 142 is connected to the system bus 134 by a secondary storage interface 144. The secondary storage devices 142 and their associated computer readable media provide nonvolatile storage of computer readable instructions (including application programs and program modules), data structures, and other data for the computing device 110.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 142 or memory 132, including an operating system 146, one or more application programs 148, other program modules 150 (such as the software engines described herein), and program data 152. The computing device 110 can utilize any suitable operating system, such as Microsoft Windows™, Google Chrome™, Apple OS, and any other operating system suitable for a computing device.

In some embodiments, a user provides inputs to the computing device 110 through one or more input devices 154. Examples of input devices 154 include a keyboard 156, mouse 158, microphone 160, and touch sensor 162 (such as a touchpad or touch sensitive display). Other embodiments include other input devices 154. The input devices are often connected to the processing device 130 through an input/output interface 164 that is coupled to the system bus 134. These input devices 154 can be connected by any number of input/output interfaces, such as a parallel port, serial port, game port, or a universal serial bus. Wireless communication between input devices and the interface 164 is possible as well, and includes infrared, BLUETOOTH® wireless technology, 802.11a/b/g/n, cellular, or other radio frequency communication systems in some possible embodiments.

In this example embodiment, a display device 166, such as a monitor, liquid crystal display device, projector, or touch sensitive display device, is also connected to the system bus 134 via an interface, such as a video adapter 168. In addition to the display device 166, the computing device 110 can include various other peripheral devices (not shown), such as speakers or a printer.

When used in a local area networking environment or a wide area networking environment (such as the Internet), the computing device 110 is typically connected to a network through a network interface 170, such as an Ethernet interface or a wireless interface. Other possible embodiments use other communication devices. For example, some embodiments of the computing device 110 include a modem for communicating across the network.

The computing device 110 typically includes at least some form of computer readable media. Computer readable media includes any available media that can be accessed by the computing device 110. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 110. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 2 is also an example of programmable electronics, which may include one or more such computing devices, and when multiple computing devices are included, such computing devices can be coupled together through a suitable data communication network so as to collectively perform the various functions, methods, or operations disclosed herein.

Figure 3:
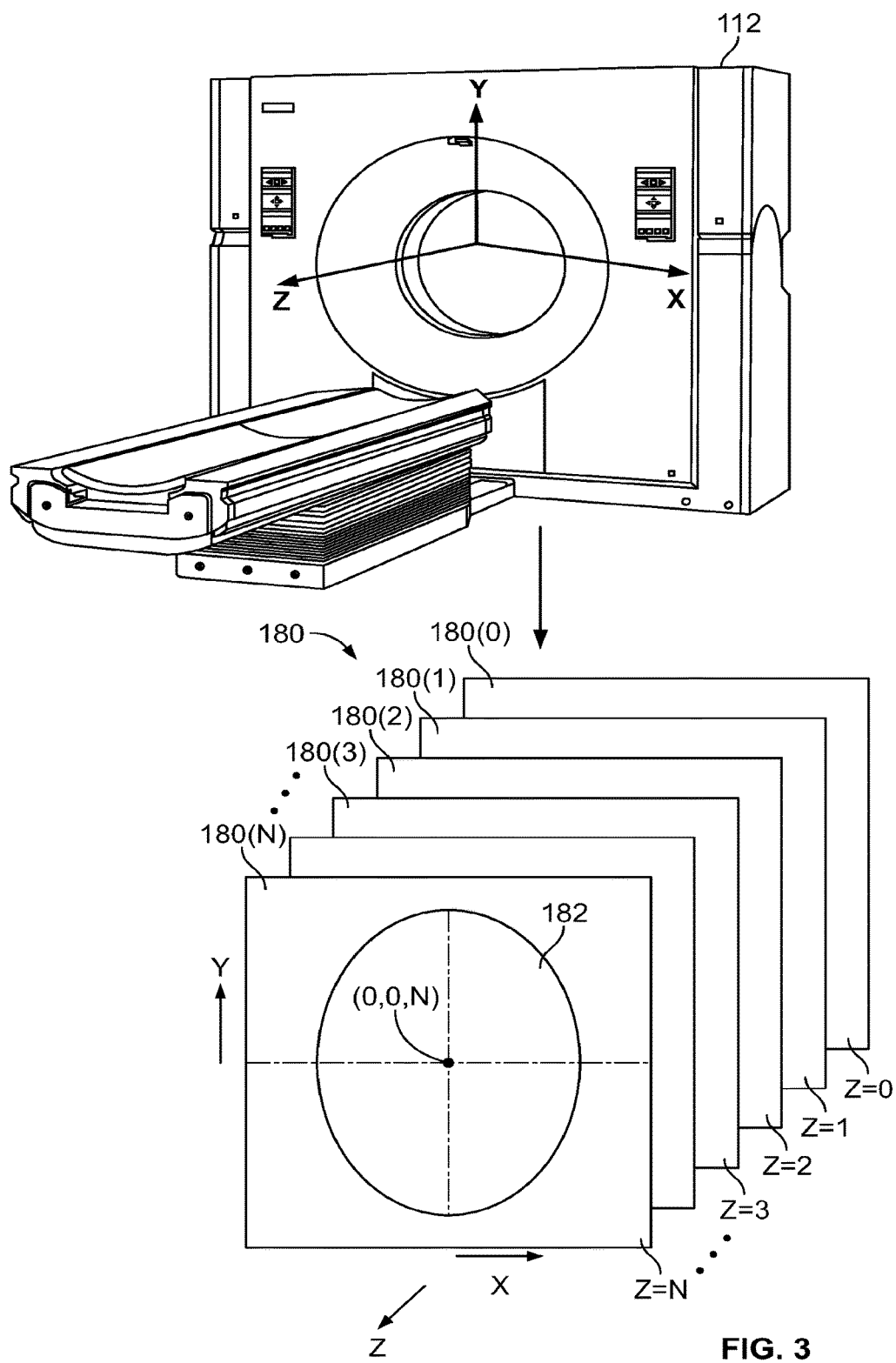
FIG. 3 is a schematic diagram illustrating an example of a scanning device and images generated by the scanning device.

FIG. 3 is a schematic diagram illustrating an example of the scanning device 112 of the system 102 (FIG. 1). Also shown are digital images 180 generated by the scanning device 112.

The scanning device 112 is a machine configured to scan a portion of a patient's body to generate digital images 180 of that portion of the body. The scanning device 112 allows medical professionals to see the structure and content of the portion of the body without a surgical procedure. An example of a scanning device is commonly referred to as a CT scanner (also sometimes referred to as a CAT scanner), which utilizes computed tomography to generate tomographic images, graphically depicting virtual slices of the scanned portion of the body. CT scanners most commonly utilized x-rays, although other electromagnetic signals may be used in other embodiments, provided that the electromagnetic signals are suitable for generating the digital images 180.

In some embodiments a patient will first undergo a simulation procedure, which may involve creating an immobilization device to keep the patient still during the anticipated radiation procedure. One example of such a device is a perforated thermoplastic mask that is molded over the head and attached to the table of the scanning device 112. Next, a fine cut CT scan is obtained by the scanning device 112 through the area of interest. For example, a scan of the whole brain can be performed. The scanning device 112 establishes a coordinate system, including an origin (typically at a location known as the "isocenter" located in the area of interest) that defines x,y,z coordinates of (0,0,0). Every part of the patient anatomy can then be expressed relative to this isocenter.

In some embodiments multiple scanning devices 112 are used. For example, the scanning device can include one or more of the CT scanner, an MRI scanner, and a PET scanner. For example, additional scans such as MRI or PET may be obtained and may be combined (fused) with the base CT scan to generate the final images used in subsequent operations discussed herein.

The images 180 are generated by the scanning device 112. In this example, the images 180 include a plurality of images (180(0-N)) each depicting a virtual slice of the area of interest 182 of the patient.

Each pixel of each image 180 corresponds with a point in space as defined by the coordinate system of the scanning device 112 (including the origin and the x,y,z axes that define the x,y,z coordinates as shown. For example, the coordinate (0,0,N) is shown in image 180(N), which is a point aligned along the z-axis with the isocenter. Therefore, the images 180 can be used to identify specific locations of features within the patient's body, and also to identify distances between two specific locations (in two or three dimensions).

Figure 4:
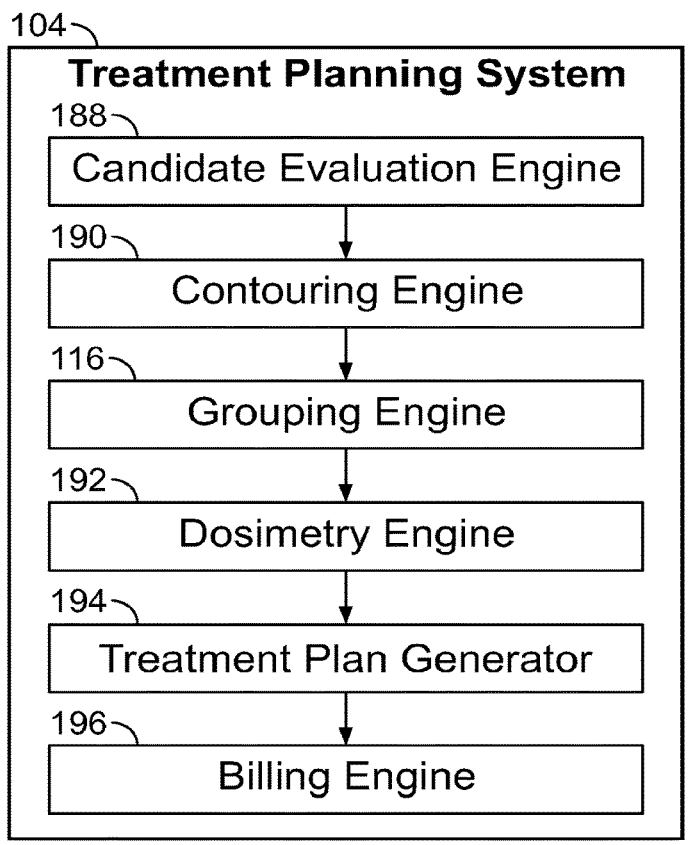
FIG. 4 is a schematic block diagram of an example of a treatment planning system.

FIG. 4 is a schematic block diagram of an example of the treatment planning system 104, shown in FIG. 1. In this example, the treatment planning system 104 includes a candidate evaluation engine 188, a contouring engine 190, the grouping engine 116, a dosimetry engine 192, a treatment plan generator 194, and a billing engine 196.

The treatment planning system 104 operates to generate a treatment plan for the treatment of multiple tumors by the radiosurgery system 106 (FIG. 1). In some embodiments the treatment planning system 104 includes a computing device 114, such as shown in FIG. 1, and an example of which is shown and described herein with reference to FIG. 2. In some embodiments the treatment planning system 104 includes more than one computing device 114, such as two or more computing devices. For example, any one or more of the engines and the generator can be executed on one or more computing devices in various possible embodiments.

In some embodiments the treatment planning system 104 includes a candidate evaluation engine 188, which operates to assist a medical professional in evaluating a particular patient to determine whether the patient's medical condition makes the patient a good candidate for radiation therapy involving grouping by the grouping engine 116.

When confronted with a patient with brain metastases, for example, there are multiple clinical parameters that would go into choosing who should be a candidate. In some embodiments the parameters include one or more of the following: number of tumors, volume of individual tumors, total volume of tumors, proximity of tumors to each other (especially whether there are large tumors in close proximity), prior brain irradiation (i.e., which would tend to raise concerns about further neural damage), life expectancy of the patient and performance status (e.g., will the patient live long enough to experience neural/cognitive damage). In some embodiments the candidate evaluation engine 188 prompts the medical professional to provide information about these parameters for the patient under consideration, and then provides recommendations to the medical professional regarding whether or not the patient is a good candidate for radiation therapy involving the grouping engine 116.

Some clinical examples of patients who may benefit from grouping include: patients with large tumors in close proximity to each other, patients with multiple brain tumors (e.g., greater than five) who wish to avoid whole brain irradiation to prevent the cognitive damage effects, patients with prior whole brain irradiation who now have a recurrence of multiple brain tumors and cannot (or should not) have whole brain irradiation repeated.

If the candidate is determined to be a good candidate, the treatment planning system 104 proceeds with further evaluation and preparation of the patient for treatment, while if the patient is not a good candidate, the candidate evaluation engine 188 may recommend that treatment of the patient using the grouping engine 116 may not be appropriate.

The contouring engine 190 is provided to identify the locations of tumors within the area of interest, such as using the images 180 generated by the scanning system 102. In some embodiments normal tissues can also be identified in the area of interest using the contouring engine 190. An example of the contouring engine 190 is illustrated and described in further detail herein with reference to FIGS. 5-7.

Contouring is the process whereby a medical professional uses the contouring tool to identify all tumors that he or she wishes to treat within the area of interest. The contouring engine allows the medical professional to draw a boundary around each tumor on every image 180 in which it is visible. This set of boundaries is called a gross tumor volume, or GTV. When the boundaries are stacked on top of each other a three-dimensional rendition of the tumor appears, and a volume can be calculated. The geometric centroid (center of mass) for each tumor can also be calculated relative to the isocenter. This process is repeated for every tumor that is to be treated, and the tumors are named (e.g., GTV1, GTV2, . . . GTVn).

The grouping engine 116 operates to assign multiple tumors (e.g., polymetastases) to multiple treatment groups. Examples of the grouping engine 116 are illustrated and described in more detail herein with reference to FIGS. 8-10.

Grouping refers to dividing up multiple tumors into multiple groups. The tumors assigned to a particular group are treated with radiation at different times than the tumors assigned to other groups. Further, in some embodiments the assignment of the tumors into separate groups involves an evaluation of the positions of the tumors with respect to each other, and assigning tumors into the groups so that tumors near to each other are in different groups, while tumors that are more significantly separated from each other may be assigned to the same group. In doing so, the areas of normal tissue in between and around the tumors end up having the radiation dose fractionated. The radiation dose to normal tissue is broken up over more days, and the normal tissue is only irradiated by the radiation beams directed to one group of tumors on any given day. This reduces the damage to normal tissues, and allows time for healing of the normal tissues to occur between treatment sessions.

The dosimetry engine 192 operates to determine appropriate radiation beam characteristics for the radiosurgery system 106. For example, in some embodiments the dosimetry engine 192 can be used to calculate how many radiation beams will be used, determine the shapes and intensities of the beams, and to determine the angles at which the beams will enter the body. In some embodiments the dosimetry engine 192 receives as an input the contouring data from the contouring engine. In some embodiments the dosimetry engine 192 also utilizes the PTV report 230, and information from the grouping engine 116 including the number of treatment groups and the identification of each tumor that is assigned to each group.

In some embodiments the dosimetry engine 192 is a dosimetry software package provided by the radiosurgery system 106 manufacturer. For example, dosimetry software packages are available for the TomoTherapy® brand radiation/radiosurgery device, the CyberKnife® brand radiosurgery device, Gamma Knife® brand radiosurgery device, and the Varian® brand linear accelerator radiation/radiosurgery devices.

The dosimetry engine 192, the grouping engine 116, and the contouring engine 190 can be separate, or any two or more can be integrated together. When separate, data can be transferred between the engines 190, 116, and 192 by utilizing a common data storage format, such as the DICOM format. In some embodiments the contouring engine 190 and the dosimetry engine 192 are modules contained within a single program. In some embodiments the grouping engine 116 is also a module contained within the single program with the dosimetry engine 192 and the contouring engine.

In some embodiments the dosimetry engine 192 automatically identifies a plurality of normal tissue dose points at locations within the patient's normal tissue, within the area of interest. Normal tissue dose points are points in the normal tissue (such as the brain) that can be used to determine appropriate radiation dosages. The dosages to these normal tissues are typically converted to biologically effective dosage (BED). The BED can be calculated with the formula: $BED=n*d*(1+d/(\alpha/\beta))$, where n is the number of treatments, d is the dose per treatment, and $\alpha/\beta$ is a constant describing how quickly a particular tissue responds to radiation. In some embodiments the BED for a selected treatment plan is used to compare groupings for several possible treatment plans to see which grouping results in the lowest summed BED overall to normal tissues. This allows for the selection of a treatment plan from several possible options that will result in the smallest biologically effective dose to the normal tissue. In some embodiments the comparison and evaluation of several treatment plans is performed by the treatment plan generator 194, discussed herein.

For example, when the area of interest is the brain, a matrix of approximately 100 to 10000 normal tissue dose points can be generated by the dosimetry engine 192 and distributed throughout the normal brain tissue (and outside of the tumors). As a more specific example, dose points can be placed at every integer centimeter coordinate within the brain tissue, for exampleat 10 mm intervals, provided that those dose points are within the brain volume, and are not contained within a PTV 218. Because the brain is approximately 1500 cc, approximately 1500 normal tissue dose points are generated according to this example.

In some embodiments the treatment planning system 104 operates to interact with one or more medical professionals to obtain or generate information including one or more of the following: (1) the type of radiosurgery system 106 to be used for treatment, i.e. one of the CyberKnife, Tomo-Therapy, TrueBeam®, Gamma Knife, or other brand radiation and radiosurgery systems; (2) a minimum and a maximum number of groupings (e.g., 1-5 is the typical range); (3) a minimum and a maximum number of fractions (e.g., 1-10 is the typical range); (4) a minimum and a maximum number of treatments (e.g., 1-30 is the typical range); (5) alpha/beta values for normal brain tissue and for tumors (e.g., default is 2 and 10) which are used to calculate BED's; (6) a nominal dose and fractionation, for example 20 Gy in 1 fraction, or 40 Gy in 5 fractions, or whatever is desired (e.g., default is 20 Gy in 1 fraction), which is converted to a BED value, or alternatively a desired BED value may be entered (default is 60Gy); (7) whether the dosage will be the same to each tumor, versus variable dosing (e.g., default is same); (8) if variable dosing is used, a separate BED or separate nominal dose/fractionation is supplied for each tumor; and (9) a typical isodose line coverage, which is approximately equal to [which percentage of the maximum dose is encompassing which percentage of the tumor volume] (default is 80% of maximum dose will cover 98% of the PTV).

Regarding item #7, for simplicity some embodiments require that all tumors be treated with the same number of fractions. This simplifies the grouping algorithm. Alternatively, a more complex grouping algorithm can be used in other embodiments that permits variable fractionation for different tumors.

Regarding item #9, the isodose line is typically in a range from 60 to 95% of maximum dose covering 90-100% of the tumor. It is presumed in some embodiments that all tumors will have the same prescribed isodose line coverage, but in other embodiments this information can be included separately for each PTV.

The treatment plan generator 194 operates to generate the treatment plan for the patient using at least some of the contouring, grouping, and dosimetry information. Following generation of the treatment plan, the radiation therapy is performed on the patient using the radiosurgery system 106 according to the treatment plan. An example of the treatment plan is illustrated and described in further detail herein with reference to FIG. 11.

The billing engine 196 operates to define billing information associated with the radiation therapy provided to the patient. In some embodiments the billing engine 196 provides the billing information to a separate billing system.

In some embodiments the billing engine 196 operates to monitor and manage billing details, and to communicate those billing details to other systems, such as to a hospital billing system. For example, currently in the United States, billing depends on the number of treatments. Stereotactic radiotherapy billing codes generally require five or fewer total treatments. If more than five treatments are used then billing codes for 3D or IMRT are used. Frequently insurance plans will also pay only for the generation of one plan.

Figure 5:
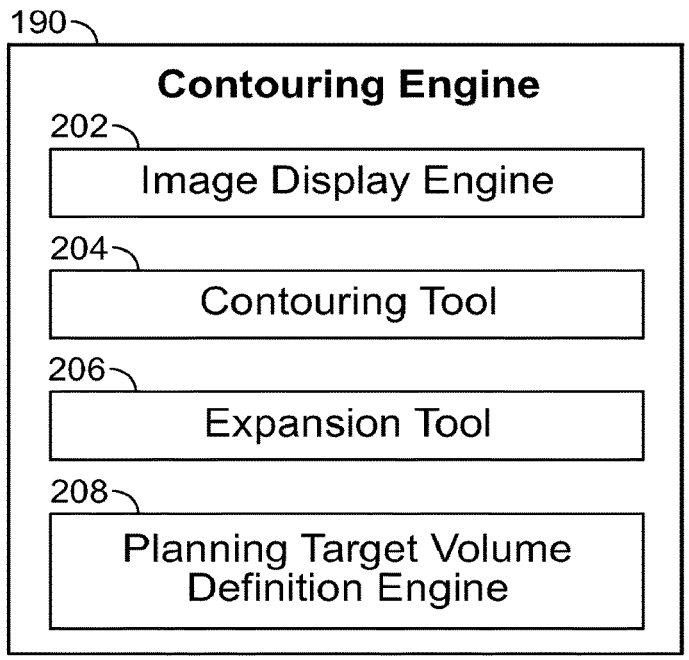
FIG. 5 is a schematic block diagram of an example contouring engine.
Figure 6:
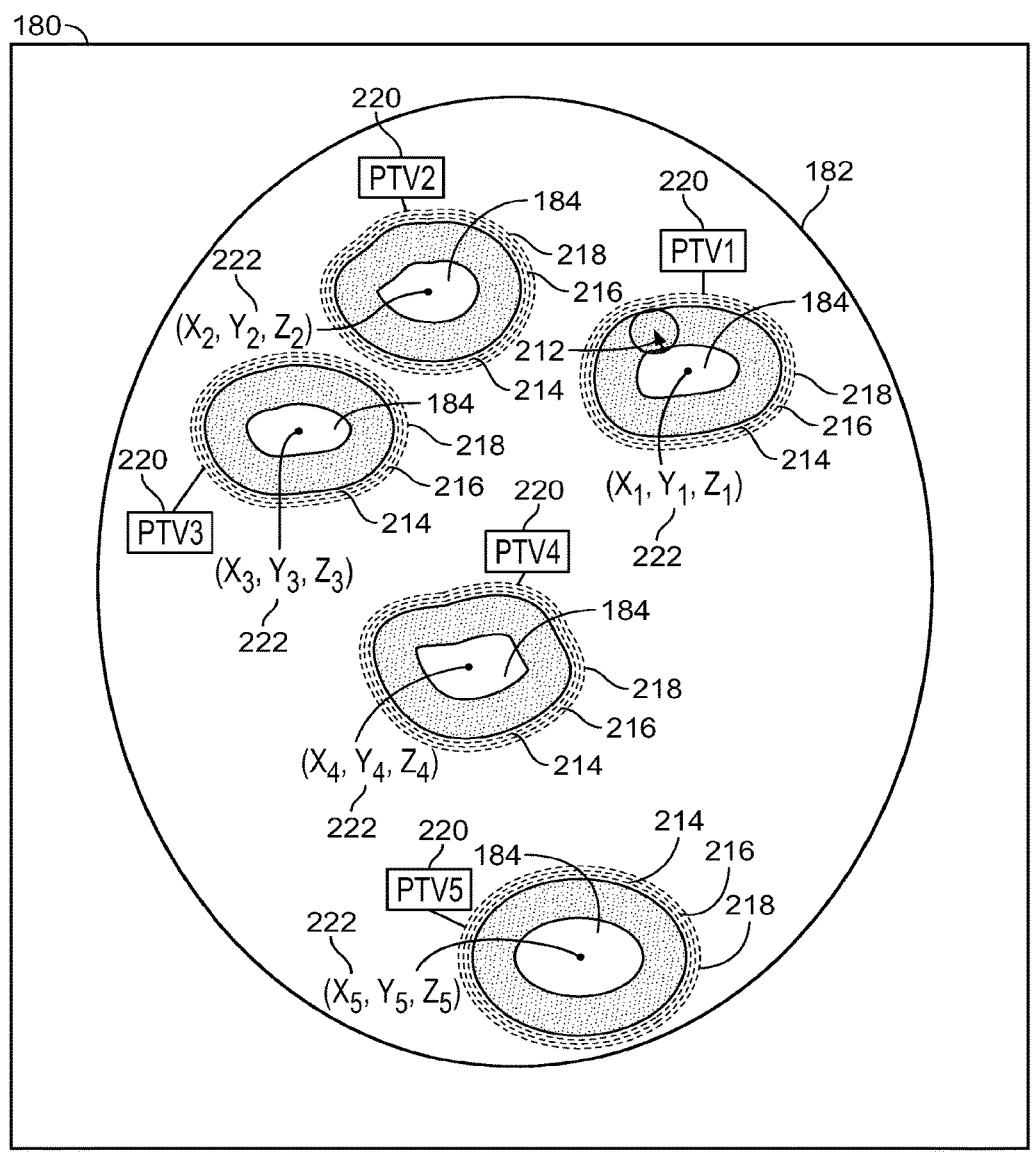
FIG. 6 is a diagram illustrating an example image depicting an area of interest of a patient, and also illustrating aspects of the example contouring engine shown in FIG. 5.

FIGS. 5-6 illustrate aspects of the contouring engine 190, shown in FIG. 4. FIG. 5 is a schematic block diagram of an example contouring engine 190, and FIG. 6 is a diagram illustrating an example image 180 depicting an area of interest 182, and also illustrating aspects of the example contouring engine 190. In this example, the contouring engine 190 includes an image display engine 202, a contouring tool 204, an expansion tool 206, and a planning target volume definition engine 208. An example of the operations performed by the contouring engine 190 is illustrated and described with reference to FIG. 6.

The contouring engine 190 receives the images 180 of the area of interest from the scanning system 102, such as by retrieving them through an electronic medical records system, a picture archiving and transmission system (PAC), by transmission across a network, or by transferring them on a computer readable storage device like a CD, DVD, or flash drive.

The image display engine 202 operates to display one or more of the images to a medical professional, such as on a display device of the computing device 114 (FIG. 1). An example of an image 180 displayed by the image display engine 202 is shown in FIG. 5.

The contouring engine 190 includes a contouring tool 204 for identifying boundaries of features in the images 180. In the example shown in FIG. 6, the contouring tool 204 uses the pointer 212 of an input device, such as a mouse. Once the contouring tool has been initiated, such as by selecting the tool from a menu, a medical professional manipulates the input device to move the pointer 212 on the displayed image 180 to identify boundaries of features of interest. As one example the features of interest are tumors. Another example of a feature of interest is normal tissue. In some embodiments normal tissue is classified as being normal or critical. Critical structures can include, for example, portions of the body that are particularly important or radiation sensitive, such as the eyes, lenses, optic nerves, parotid glands, oral cavity, brainstem, hippocampus, etc. Normal tissues, including critical structures, are sometimes referred to as organs at risk (OARs). Normal structures can also be assigned unique identifiers for ease of reference, such as "BRAIN" or other identifier, such as "OAR1" to "OARN" (organ at risk number 1, number 2, etc.)."

In some embodiments normal tissue dose points are also identified by the medical professional. For example, when the area of interest is the brain, in some embodiments the medical professional utilizes the contouring tool 204 to identify about twenty or more normal tissue dose points throughout the brain, which are identified with labels such as NDP1 to NDPn. In some embodiments the normal tissue dose points are represented by a circle on a single image 180, such as a circle having a diameter of 3 mm. These are located in-between pairs of adjacent tumors, in critical areas of brain (such as the hippocampus), and at various landmarks, points or intervals in the midline of the brain, for example. In another possible embodiment the normal tissue dose points are automatically generated, such as by the dosimetry engine 192, discussed in further detail herein. For example, a matrix of approximately 100 to 10000 normal tissue dose points can be generated by the dosimetry engine 192 and distributed throughout the normal tissue (and outside of the tumors).

In some embodiments, automated or partially automated processes can be used to identify boundaries of features. For example, image processing can be performed to identify the boundaries using one or more digital image edge detection algorithms.

The contouring tool 204 is used to identify boundaries of the tumors in the area of interest 182 in each image 180 in which the tumors are visible. The boundaries define the gross tumor volume (GTV) 214.

After all desired features have been contoured by the contouring tool in all images 180 in which these features appear it is possible to use an expansion tool. The expansion tool 206 operates to expand the boundaries around a tumor, such as to add a safety margin around the features.

In some embodiments, the expansion tool 206 defines an additional safety margin around the GTV 214 to define the clinical target volume (CTV) 216. The CTV 216 is a second volume that contains the GTV 214, plus a margin for invisible (microscopic) tumor extensions beyond what is visible to the medical professional in the images 180. This additional area is important because it must be adequately treated to fully eliminate the tumor from the patient. In some embodiments the expansion tool 206 prompts the medical professional to identify the desired margin distance for the CTV 216, and the expansion tool 206 then computes boundaries of the CTV 216 by expanding the boundaries by the margin distance.

In some embodiments the expansion tool 206 defines a safety distance around the GTV 214 or the CTV 216 to define the planning target volume (PTV) 218. The PTV 218, allows for uncertainties in planning or treatment delivery, such as inaccuracies in setting up the patient, or patient or organ motion during treatment. It is a geometric concept designed to ensure that the radiotherapy dose is actually delivered to the CTV 216, for example.

In some embodiments the PTV 218 is defined by adding a single safety margin to the GTV 214 without defining the CTV 216. Typically very small safety margins are added to each GTV 214. In one example, the safety margin distance is in a range from greater than 0 mm to 5 mm, and more typically between greater than 0 mm to 2 mm. The PTV equals the GTV+any additional margins.

Furthermore, radiotherapy planning will typically involve an evaluation of whether any normal tissues are present in the area, and whether those tissues are critical normal tissues or other organs at risk, for which radiation exposure should be minimized or avoided. In some embodiments the expansion tool 206 operates to add a margin analogous to the PTV margin around some or all of the normal tissues to ensure that the organ cannot receive a higher-than-safe dose. For example, an organ such as the spinal cord may be a critical and highly radiation sensitive organ for which a severe clinical manifestation would result if it received a higher-than-safe dose of radiation. Upon the expansion of the normal tissue boundary by the safety margin, a planning organ at risk volume is defined. For simplicity, boundaries for the normal tissues (such as surrounding the tumors 184 and within the area of interest 182) are not illustrated in FIG. 6.

The planning target volume definition engine 208 operates to define the planning target volume 218 using the data generated by the contouring tool 204 and the expansion tool 206. For example, in some embodiments the planning target volume definition engine 208 uses the two-dimensional PTV 218 definitions to generate three-dimensional information for the PTV 218. In some embodiments the planning target volume definition engine 208 operates to perform one or more of the following steps: generate an identifier 220 (such as a label or number) to uniquely identify each of the tumors and associated PTV's 218, determine a three-dimensional volume of each PTV 218 associated with each tumor 184, and determine a centroid coordinate for each PTV 218.

An example of the identifier 220 is a sequential label applied to the PTV's 218, such as "PTV1," "PTV2," . . . "PTVN," where N is the total number of tumors in the area of interest 182. The identifiers can be defined in any desired order, such as based on location (e.g., in order from front to back/left to right), based on volume (e.g., largest to smallest), or any other desired order.

The three-dimensional volume of the PTV can be computed using the known correspondence between the pixels in the digital images 180 and the actual locations of the corresponding features in the body, such as using the coordinate system established by the scanning device 112. The two-dimensional shape of each PTV 218 is known for each image 180, and each image corresponds to a slice having a thickness corresponding to the distance between each slice along the z-axis (FIG. 3). The three-dimensional volume of the PTV 218 can be computed based on this information.

Additionally, a centroid coordinate 222 is also computed for each PTV based on the known three-dimensional shape and position of the PTV 218. For example, PTV 1, shown in FIG. 6, has a centroid coordinate 222 of (x5, y5, z5), where x5, y5, and z5 represent the distances of the centroid from the isocenter along each of the x, y, and z axes, respectively.

In some embodiments the planning target volume definition engine 208 generates a PTV report containing data regarding each tumor 184, such as shown in FIG. 7.

FIG. 7 is a schematic block diagram illustrating an example PTV report 230, such as generated by the planning target volume definition engine 208, shown in FIG. 5.

The PTV report 230 is generated and saved in a computer readable storage device, and can be stored in a variety of possible formats, as desired, such as in a spreadsheet file format. In this example, the PTV report includes a plurality of rows and columns. Each row is associated with one of the tumors 184 (FIG. 6), and each column provides additional information about the respective tumor 184. In some embodiments the PTV report 230 is in a digital imaging and communications in medicine (DICOM) file format.

In this example the planning target volume report includes information about each PTV 218. For example, the PTV report 230 includes the PTV ID 220 ("PTV1" to "PTV5") for each tumor 184 (FIG. 6) in the area of interest 182 the PTV ID 220.

In some embodiments the PTV report 230 identifies centroid coordinates 222 for each tumor. For example, the PTV report 230 indicates that PTV1 220 has a centroid coordinate of (x1, y1, z1).

In some embodiments the PTV report 230 indicates the volume of the tumor 184. For example, the PTV report 230 indicates that PTV1 220 has a volume V1.

The output of the contouring engine 190 includes the PTV report 230. In some embodiments additional information can also be output from the contouring engine 190, and such information can either be included as part of the PTV report 230, or can be provided separate from the PTV report 230, such as in one or more additional reports.

In some embodiments the output from the contouring engine 190 includes one or more of the following: a quantity of PTVs, the PTV identifiers 220, the PTV volumes 232, the PTV geometric centroid coordinates 222, the coordinates of all identified normal tissue dose points, the brain volume, the brain geometric centroid coordinate, a set of coordinates describing the entire brain shape, and combinations thereof. In some embodiments an idealized brain shape can be used in some embodiments in place of the coordinates describing the entire brain shape. This example relates to an area of interest in which the normal tissue is the brain. Other regions of the body can also be used in other embodiments, in which case the respective features of other normal tissues can be identified instead of the features of the brain listed in this example. Examples of other normal tissues include a lung, the liver, or other radiation sensitive organs.

In some embodiments the information output from the contouring engine 190 is provided in one or more files, such as in the DICOM file format. In other embodiments the information can be output in other formats, such as a spreadsheet or comma delimited file, or manually entered into a spreadsheet by a medical professional by viewing the information from a printout or on a display device.

FIG. 8 is a flow chart illustrating an example method 240 of grouping tumors. In this example the method includes operations 242, 244, and 246. In some embodiments the method 240 is performed by the grouping engine 116, shown in FIGS. 1 and 4.

The operation 242 is performed to determine a quantity of tumors to be treated by the radiosurgery system 106 (FIG. 1). In some embodiments the quantity of tumors is obtained from an output of the treatment planning system 104, such as in the PTV report 230, shown in FIG. 7, or in another form. In another possible embodiment, the operation 242 prompts a medical professional to enter the quantity of tumors.

Because the grouping algorithm involves the grouping of multiple tumors, the quantity of tumors is greater than one. Typically the quantity of tumors is greater than 3. Although the grouping algorithm could be used for any large number of tumors, most typically it would be used with patients having 100 tumors or less, and more typically with patients having 50 tumors or less. In some embodiments the quantity of tumors is in a range from 3 to 100 tumors, or from 3 to 50 tumors. In other embodiments the quantity of tumors is in a range from 4 to 100 tumors, or from 4 to 50 tumors. In yet other embodiments the quantity of tumors is in a range from 5 to 100 tumors, or from 5 to 50 tumors. Other embodiments involve other quantities of tumors.

The operation 244 is performed to determine a quantity of treatment groups.

In some embodiments the operation 244 prompts the user to enter a number of treatment groups, and in other embodiments the operation 244 computes a suggested number of treatment groups. In some embodiments the number of treatment groups is in a range from 2 to 10. In some embodiments the quantity of treatment groups is in a range from 2 to 5, which will typically be sufficient for the treatment of up to 50 tumors. Other quantities of treatment groups are possible in other embodiments.

As discussed herein, tumors assigned to separate treatment groups are treated in different treatment sessions, and such treatment sessions typically occur on different days or may occur on the same day as long as they are separated by a sufficient number of hours to allow repair of normal tissues. Therefore, the number of treatment groups also corresponds to a minimum number of treatment sessions that will be needed for the therapy. Therefore, selection of the quantity of treatment groups involves a consideration of the number of desired treatment sessions for the patient. Further, in some embodiments fractionation is also used as discussed herein, which involves dividing a total dose into multiple treatment sessions. Accordingly, when grouping and fractionation are both used, the number of treatment sessions is the number of groupings multiplied by the number of fractions. For example, a dose that is fractionated into two fractions, may involve twice as many visits as the non-fractionated dose.

In view of this, although it may be beneficial to use a large quantity of treatment groups, doing so can be inefficient, leading to too many visits, which is inconvenient to the patient and requires a great deal of medical resources that do not provide a significant benefit to the patient's health. The reduction in the biologically effective dose to normal brain tissue, for example, will be of diminishing returns with more and more groups. The largest benefit occurs going from no treatment groupings to two treatment groups, with smaller further benefits occurring with the addition of each additional treatment group.

In some embodiments the operation 244 generates and suggests to the medical professional a recommended quantity of treatment groups. In one possible embodiment, a lookup table is used, which identifies a predetermined quantity of groups for particular quantities of tumors. In another possible embodiment, the operation 244 evaluates tumor data, such as from the PTV report 230, to generate a recommended number of treatment groups. For example, in some embodiments the operations 244 and 246 can be performed for every possible quantity of treatment groups (such as within a predetermined range of quantities of treatment groups, such as in a range from 2 to 5 groups). Simulations or computations can then be performed to determine various characteristics of the proposed groupings, and used to select a preferred quantity of treatment groups. In some embodiments the selection of the preferred quantity of treatment groups is done automatically, such as by comparing the characteristics to predetermined factors (e.g., to minimize radiation exposure to normal tissue, or to reduce the number of visits, or other criteria). In another embodiment the various characteristics are presented to the medical professional who considers the relevant factors and identifies a preferred quantity of treatment groups.

The operation 246 is performed to assign tumors to the treatment groups.

In some embodiments the operation 246 simulates all of the possible options and determines the most preferred assignment based on one or more predetermined factors. Depending on the factors, there will typically be one solution that best aligns with those factors. The solution will typically be different for different radiosurgery devices 120 and treatment planning systems 104, due to differences in their operation and limitations of beam types, quantities, sizes, and positions, for example.

To illustrate one example, if there are 50 tumors and 5 treatment groups, there are $5^{50}$ (or $8.8 \times 10^{34}$) possible combinations of tumor groupings. It would be time consuming and require substantial resources to run simulations of all of these possible combinations. Therefore, in some embodiments a grouping algorithm is used to determine a reasonable approximation of the ideal solution, rather than considering all possible assignment combinations. An example of the operation 246 is illustrated and described in further detail with reference to FIG. 9.

In some embodiments the assigning of tumors to treatment groups in operation 246 is performed wherein a quantity of the treatment groups is less than a quantity of the tumors. (For example, as discussed with reference to FIG. 10, three tumors may be assigned to two treatment groups, such that at least one of the treatment groups has two or more tumors. In some embodiments at least one of the treatment groups is assigned at least two tumors.

Figure 9:
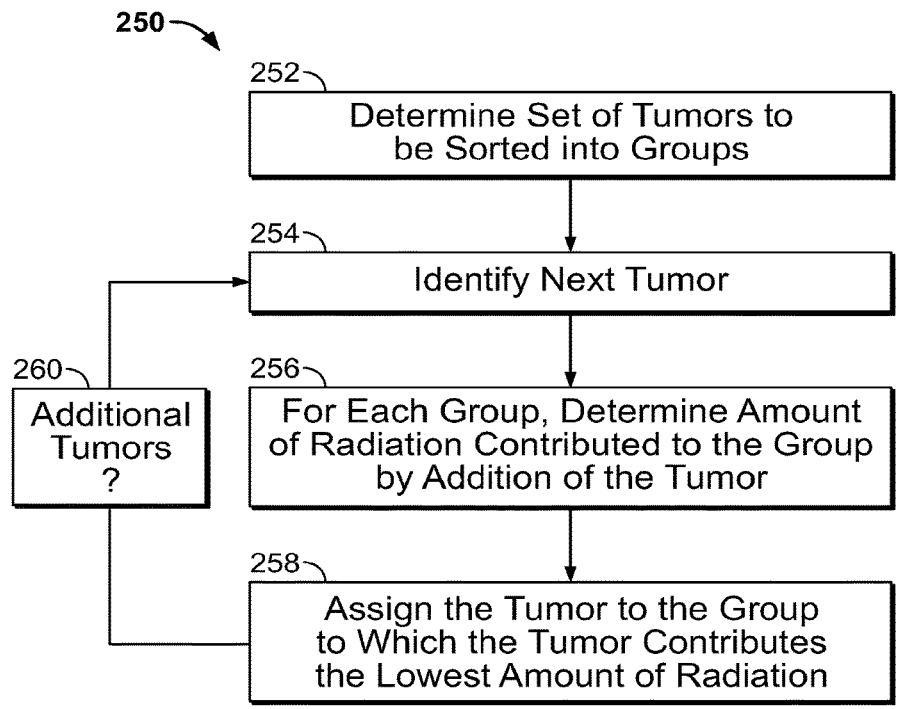
FIG. 9 is a flow chart illustrating an example method of assigning tumors to treatment groups.

FIG. 9 is a flow chart illustrating an example method 250 of assigning tumors to treatment groups. In this example the method 250 includes operations 252, 254, 256, and 258. The method 250 is an example of the operation 246, shown in FIG. 8.

Operation 252 is performed to determine a set of tumors to be sorted into tumor groups. As one example, operation 252 involves receiving or accessing the PTV report 230 or the information contained therein identifying each of the tumors in an area of interest. Information regarding the tumors can also be obtained in other ways in other embodiments. In some embodiments the operation 252 also involves the identification of the quantity of groups into which the tumors will be assigned. In this example operation 252 has determined that there are G groups, where G is the quantity of groups.

In order to sort the tumors into different groups, they are considered one by one. Once the set of tumors has been identified, the operation 254 is performed to identify a next tumor in the set to be sorted into the groups. The operation 254 involves the determination of an order in which the tumors should be processed. There are various orders in which the tumors can be processed. One option is to process the tumors according to volume, starting with the tumor having the largest volume and ending with the tumor having the smallest volume. Another option is to sort the tumors sequentially based on the tumor ID, such as the PTV ID 220, shown in FIG. 7. In this case, the tumors are processed sequentially from PTV1 to PTVN. Another option is to process tumors according to dose impact, starting with the tumor having the largest dose impact and ending with the tumor having the smallest dose impact. Dose impact is described in further detail herein. A further option is to sort tumors randomly. As one example, the tumors can be sorted using a Monte Carlo algorithm, also discussed in further detail herein. Other embodiments utilize other orders for processing tumors in operation 254.

One method of evaluating the impact of adding a tumor to a group of tumors involves the determination of the tumor's dose impact on other tumors. The dose impact analysis utilizes an analogy, referred to as the shining light analogy, in which each tumor is considered to act like a source of radiation. Dose impact refers to the amount of radiation at any given point being emitted from a tumor and added to the amount of radiation reaching that point from all other tumors. In some embodiments the dose impact of any given tumor is approximated using the following formula:

$$\text{Dose impact} = k * \text{dose} * \text{area} * 1/\text{distance}^{(2-ai)}$$

where k is a constant and ai is the axial index which ranges from 0 to 1 and is discussed further below. As long as the point being evaluated is not within the boundaries of a tumor. In some embodiments volume$^{2/3}$ is substituted for area. In some embodiments, the distance exponent may be 2. In some embodiments the distance exponent may be less than 2 (between 1 and 2) if the beam set is preferentially in an axial or other 2-dimensional direction. In some embodiments the dose impact result will be modified if the beam set from the tumor being evaluated cannot reach or only partially reaches the evaluation point. Examples that follow may use distance$^2$ but it is understood that the exponent may vary from 1 to 2.

Although the following description of the shining light analogy refers to the brain as the area of interest, the same principles also apply to other portions of the body.

In stereotactic radiosurgery, an array of beams or beam arcs will enter the skull from multiple angles. As these beams pass through the skull they each gradually widen, similar to how a flashlight beam widens with distance. At the same time the radiation is also gradually being absorbed by the tissues and the beam becomes attenuated. Each beam has been shaped so that by the depth at which it reaches the tumor it will approximate the shape of the tumor, or may be smaller than the face of the tumor. A tumor can be visualized as having dozens or hundreds of beams crisscrossing it. Where all the beams converge and cross at the tumor the highest dose is being delivered. However, at further and further distances away from the tumor the intensity of the radiation passing through the tissues will rapidly decrease as fewer beams overlap. Larger tumors with a larger cross-sectional area will obviously require larger beams, creating a higher dose of radiation in the normal tissues. If there are several tumors in the brain, each tumor will have its own array of beams entering the skull and intersecting upon it. There will therefore be regions in the brain where separate beams targeting two separate tumors are passing through the same tissue, locally increasing the absorbed dose to healthy brain in those areas. These areas of significant beam overlap will worsen if the tumors are closer together, and if the tumors are larger in size. The shining light analogy can be used for assigning tumors into different groups such that the dose at any point will depend on the distance to that tumor, and the tumor cross-sectional area, and the dose. This can be approximated as k*volume$^{2/3}$*1/distance$^2$*dose. The dose contribution from every tumor can be summated for any point in the brain. If all tumors are receiving the same prescribed dose then the dose factor can be dropped from the grouping formula. In addition, for determining grouping, k can be dropped from the formula as well, leaving the most important parameters, volume$^{2/3}$*1/distance$^2$.

The shining light analogy works by imagining that every tumor is actually a source of radiation beams or light beams. Instead of the radiation beams being aimed at the tumor, they are being emitted in all directions. A single tumor will emit radiation to the entire brain, with the amount of radiation reaching any point in the brain dependent on the tumor radiation dose, tumor size, and how close that point is to the tumor.

An example is shown in FIG. 9 by operations 256 and 258.

The operation 256 is performed to evaluate the next tumor (identified in operation 254), and to determine, for each group, the amount of radiation contributed to the group by the addition of the tumor, as well as how much dose the existing tumors in the group are imparting on the tumor being considered for addition. In other words, if the tumor is added to that group, operation 256 determines the amount of additional radiation exposure the existing tumors and the tumor being considered will impart on each other. In some embodiments, this dose is calculated at intermediary point(s) in between pairs of tumors.

As discussed above, one way to determine the amount of radiation contributed is by computing a sum of (volume$^{2/3}$*1/distance$^2$*dose) for each tumor previously assigned to a group. If the same dose is used for each tumor, then the formula may be simplified to the sum of (volume$^{2/3}$*1/distance$^2$). Volume represents the volume of the tumor PTV under evaluation (e.g., the tumor identified in operation 254), and distance represents a distance between the tumor and the point of interest. In some embodiments distance is calculated from the center of the tumor, in others it is taken from the edge of the tumor, in others it is taken from some intermediary point between these two values.

The operation 258 is then performed to assign the tumor to the group to which the tumor contributes the lowest amount of radiation.

Operation 260 is then performed to repeat operations 254, 256, and 258 until all tumors have been assigned to the groups.

In operation 256, if a group has not yet been assigned any tumor, then the amount of radiation contributed to that group is considered to be zero. In operation 258, if the amount of radiation contributed to two or more groups is the same, such as before any of the tumors have been assigned to a group, then the tumor can be assigned to either group. In some embodiments a default assignment rule is used, such as to assign the tumors based on a sequential order of group ID's (e.g., G1, G2, G3) assigned to each group. For example, the first tumor processed by operation 250 will be assigned to Group G1 and the second tumor will be assigned to Group G2, etc. until all groups contain at least one tumor.

In some embodiments the formula utilized in operation 256, and discussed above, is modified by one or more beam delivery parameters, which will be discussed in further detail.

In another embodiment, the tumors are grouped by analyzing the midway dose impact, the radiation impact on the tissue located halfway between two tumors. This is calculated with the following formula:

$$\text{Midway Dose Impact} = (K * \text{dose1} * \text{area1} + k * \text{dose2} * \text{area2})/(0.5 * \text{distance})^2$$

The midway impact dose can be calculated between one tumor and all the tumors within a given group, and those midway impact doses can be summed to determine the summed midway dose impact for that tumor. Additionally, the group midway dose impact can be calculated by summing all the midway dose impacts for all the pairs of tumors within a given group. The group midway dose impact can then be converted to group midway BED impact. The group midway BED impact for all the groups can be summed to determine the all groups midway BED impact. The tumors are first sorted by having their total summed midway dose impact calculated with every tumor to be treated. The tumors with the largest total summed midway dose impacts are placed into G groups. The tumor with the next highest total summed midway dose impact can then have the summed midway dose calculated with the tumors that have already been placed into each of the groups. The tumor is placed into the group with the lowest summed midway dose impact. The process is repeated for each tumor, in decreasing order of total summed midway dose impact, until all the tumors have been grouped. Different grouping solutions can also be compared by comparing the all groups midway BED impact, where the summed midway doses are converted into BED values, and are summed in turn. The grouping that results in the lowest all groups midway BED impact could be selected for the treatment plan. In other embodiments, other points or multiple points can be used to evaluate dose impact, for example the average dose impact along a line connector between 2 tumors.

In an idealized model, there are an infinite number of beams that are directed at the tumor from all possible directions. In reality however, there are a finite number of beams and they enter the skull from a limited set of allowable angles. With the TomoTherapy brand radiosurgery system, for example, the beams only come from the axial direction, i.e. at right angles to the long axis of the body. "Tomos" comes from Greek, and means a slice. When using the TomoTherapy brand radiosurgery device, the grouping algorithm is modified so that there is greater emphasis on avoiding having tumors placed in the same group that also happen to be in the same axial (Z) plane. This can be accomplished by modifying the dose impact formula such that it considers whether beams that are targeting a specific tumor are capable of reaching the evaluation point. With TomoTherapy for example, only if the point being evaluated is located within the minimum and maximum Z coordinate of a tumor (+/−a penumbra & dose falloff value) will there be a significant dose impact.

Many radiosurgery devices also have beams entering the skull from non-axial directions, but axial or near-axial directions are still often favored. Each radiosurgery device can therefore have an associated value that describes the preponderance of beams from the axial direction. For a TomoTherapy brand radiosurgery device this axial index would be 1.0, for an idealized model the value would be 0.0. For a radiosurgery device such as the CyberKnife brand radiosurgery device the value may be estimated at 0.2 and for the Gamma Knife radiosurgery device the value may be estimated at 0.1. These values are estimates and the real numbers can be easily ascertained.

With radiosurgery devices that allow non-axial beam angles, there are often more beams that enter from the superior (cranial) direction rather than an inferior (caudal) direction. For example, a beam would not enter by the feet and travel through the body to reach the brain. In the Gamma Knife brand radiosurgery device, for example, individual beams are directed via a helmet and enter from predominately axial and superior directions. An index value ranging from −1 to +1 may be used to describe to whether the beams preferentially enter from inferior (−1), ideally balanced (0), or cranial (+1). This parameter is less important than the axial index value, since a beam that enters superiorly will still pass through the tumor and irradiate tissues inferiorly. However because the beam energy is gradually absorbed as it passes through tissue the dose will be lower in the tissues beyond (inferior to) the tumor.

Another parameter deals with avoidance of certain anterior/posterior beams passing through the eyes and oral cavity, as well the inability of some radiosurgery devices such as CyberKnife brand radiosurgery device to direct beams from a posterior direction below the patient. This results in right & left preference over ant & post, and also an anterior >posterior preference for the CyberKnife brand radiosurgery device.

In some embodiments the method 250 utilizes a specified axial preference index value (ai), and optionally what the other beam parameters are, depending on the radiosurgery device 120 to be used. These may be provided by prompting the medical provider, or input in a report or other manner, for example. In some embodiments the parameters are preloaded for each radiosurgery device so that the medical provider can simply select the radiosurgery device to allow the system to lookup the parameters associated with the radiosurgery device. In some embodiments, a complete description of the machine-specific and organ-specific allowable beam set is provided. For example, multiple points (also called nodes) can evenly be spaced on the surface of a sphere, and each of these points can contain information regarding the probability of a beam existing in the vector from that point to the center of the sphere.

Figure 10:
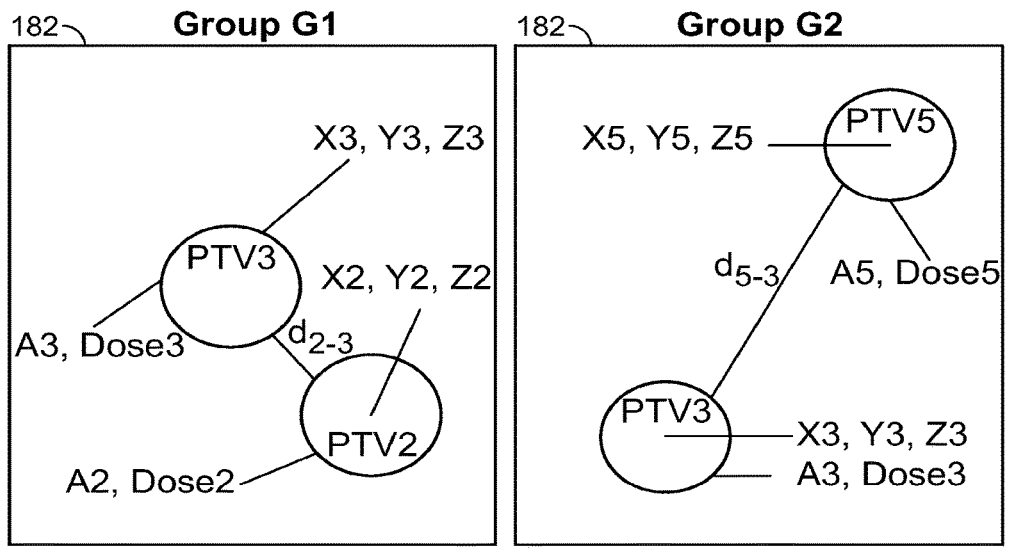
FIG. 10 is a diagram illustrating an example method of assigning a tumor to a tumor group.

FIG. 10 is a diagram illustrating an example method of assigning a tumor to a tumor group. This example illustrates the evaluation of a tumor PTV3 to determine whether the tumor PTV3 should be included in group G1 or group G2. In this example, group G1 has already been assigned a tumor PTV2, and group G2 has already been assigned a tumor PTV5. The tumors are shown in the area of interest 182, such as the brain.

In this example, after the assignment of tumors PTV2 and PTV5, tumor PTV3 is determined to be the next tumor for evaluation (e.g., see, operation 254, FIG. 9).

The tumor PTV3 is located at a centroid coordinate (x3, y3, z3), has an area A3, and is assigned a dose $DOSE_3$.

To determine whether to assign the tumor PTV3 to group G1 or group G2, both groups are evaluated to determine the summed midway dose impact for tumor PTV3 when it is added to each group.

Group G1 currently includes a single tumor PTV2. This tumor has a centroid coordinate of (x2, y2, z3), an area A2, and is assigned a dose DOSE2. A distance between the tumor PTV2 and the tumor PTV3 is $d_{2-3}$.

To determine the summed midway dose impact for tumor PTV3 in each group, the formula:

$$\text{Midway Dose Impact} = (K^*\text{dose1}^*\text{area1} + k^*\text{dose2}^*\text{area2})/(0.5^*\text{distance})^2$$

is calculated. The volume and dose parameters are of PTV3 and PTV2. The dose variable can be dropped if the doses are the same. Additionally, k is a constant and can also be dropped. Therefore, the result is:

$$(A3+A2)/(0.5^*d_{2-3})^2$$

Turning to group G2, it currently also includes a single tumor PTV5. This tumor has a centroid coordinate of (x5, y5, z5) and an area A5. A distance between the tumor PTV3 and the tumor PTV5 is $d_{3-5}$.

To determine the summed midway dose impact for tumor PTV3 in group G2 the formula:

$$(A3+A5)/(0.5^*d_{3-5})^2$$

is used.

In this example, the distance $d_{2-3}$ is much less than the distance $d_{3-5}$, and the tumors are of similar volume, so as a result the tumor PTV3 would result in a much higher summed midway dose impact with PTV2 then with PTV5. Accordingly, the tumor PTV3 is assigned to group G2.

Figure 11:
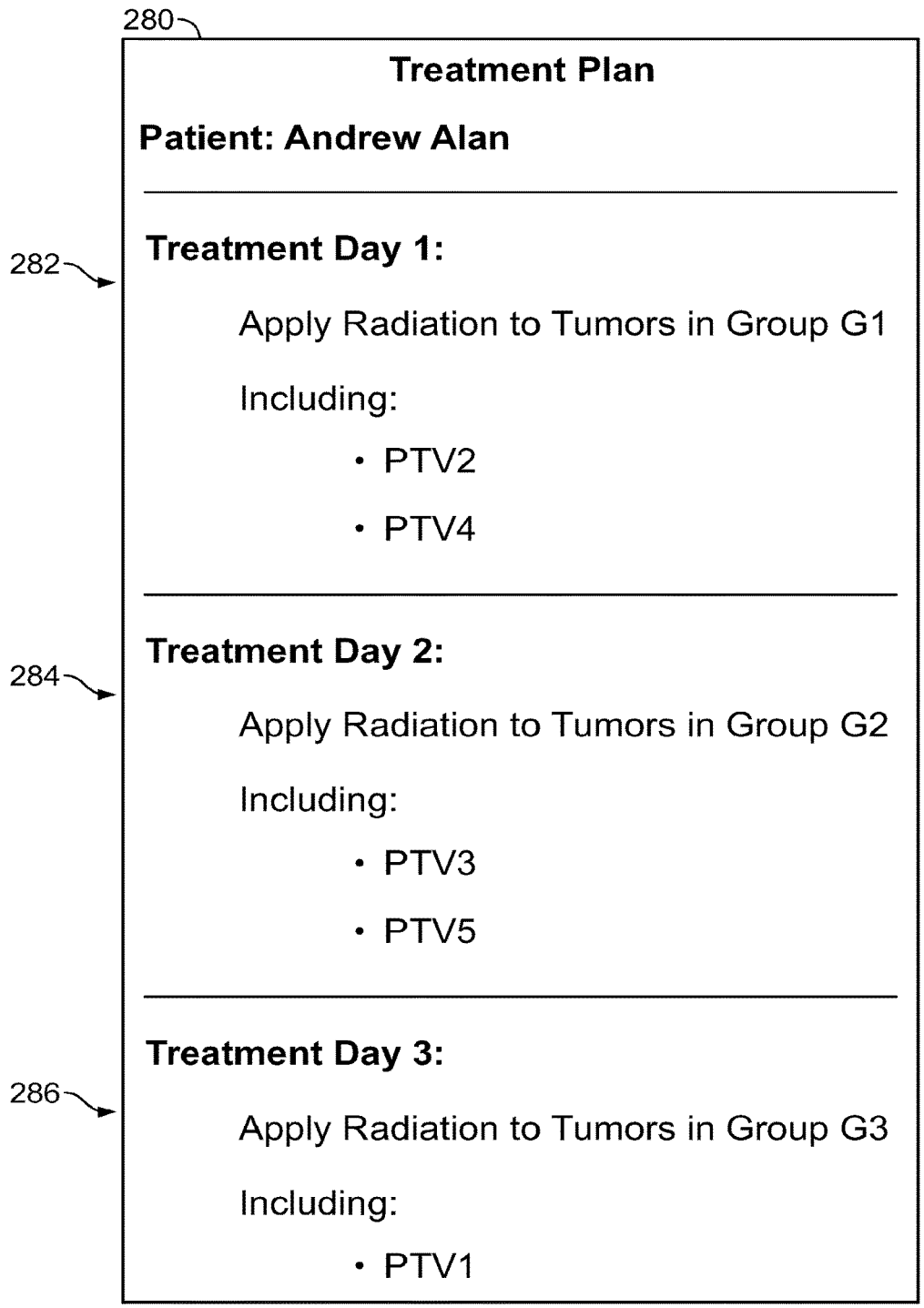
FIG. 11 is a schematic diagram illustrating an example of a treatment plan.

FIG. 11 is a schematic diagram illustrating an example of a treatment plan 280, such as generated by the treatment plan generator 194, shown in FIG. 4, for a patient (e.g., patient Andrew Alan).

In this example, a treatment plan has been generated to treat five tumors (PTV1 to PTV5) that have been assigned to three groups (G1 to G3). The treatment plan 280 includes a listing of treatment sessions, including a plan 282 for treatment day 1, a plan 284 for treatment day 2, and a plan 286 for treatment day 3.

The plan 282 for treatment day 1 indicates that two tumors will be treated on this day, including PTV2 and PTV4.

Similarly, the plan 284 for treatment day 2 also indicates that two tumors will be treated on this day, including PTV3 and PTV5.

The plan 286 for day 3 indicates that a single tumor PTV1 will be treated on this day.

Referring briefly back to FIG. 6, by separating the treatment of the tumors into separate groups, the treatment plan 280 allows normal tissue between tumors to heal before adjacent tumors are treated. For example, by separating the adjacent tumors PTV2 and PTV3 into separate groups and, as a result, treating those tumors on different days, the normal tissue between PTV2 and PTV3 is prevented from receiving excessive radiation in a single session, which may otherwise occur if both tumors were treated on a single day. Stated another way, by treating the tumors PTV2 and PTV3 on separate days, the amount of radiation applied to the individual tumors can be increased because the normal tissue therebetween has time to heal between sessions. If the tumors were treated in a single session, the amount of radiation that could be applied to the tumors would have to be reduced to avoid overexposing the normal tissue. Although the total dose received by the normal tissues summed over all the treatments is similar, that dose has now been subdivided because of tumor grouping, and the amount of damage is thereby reduced according to the BED equation.

Therefore, some embodiments that utilize the grouping of tumors as discussed herein, one or more of the following advantages may be realized: (1) each group of tumors can be treated in a full single dose, but the dosage to the intervening normal tissue becomes fractionated, (2) the BED to normal brain tissue can be reduced by up to 40% (based on experimental dosimetry assessment), without reducing BED to tumors, (3) grouping may be more powerful than temporal fractionation in sparing normal brain tissue, (4) grouping and temporal fractionation may be combined together to create spatial-temporal fractionation, and the benefits may be additive; and (5) dividing multiple tumors into groups allows treatment sessions to be shorter and more tolerable in length for the patient.

In addition to daily treatment plans, in some embodiments it is desirable to combine grouping with fractionation. In other words, a dose of radiation intended for the tumors in one group (e.g., group G1) can be divided into multiple fractions that are given on separate days. So, for example, the treatment plan shown in FIG. 11 could be combined with fractionation to apply half of the dose in each of days 1 to 3, and then to repeat the plan to apply the remaining half of the dose on days 4 to 6. The number of treatments will equal the number of groups multiplied by the number of fractions.

In most cases treatment sessions will occur not more than once per day (rather than having two or more treatment sessions in a single day) in order to allow adequate time for the normal tissue to heal. For example, this can be desirable due to the relatively slow central nervous system repair time of radiation sublethal damage. However, in an alternate embodiment more than one treatment can be performed on a single day if there is a suitable time interval between treatments, for example greater than 6 hours, to allow for repair of normal tissues. The following example will illustrate a treatment plan where only one treatment is given per day, but this example is not intended to be limiting.

Typically, a treatment plan involving both grouping and fractionation will schedule the application of all fractions in a single group before moving onto the next plan/group. This is in order to keep fractionation on a daily basis. It also helps avoid errors by only treating one plan at a time. If it is the usual practice of the medical professional is to treat stereotactic radiotherapy patients every 2 or 3 days, and if there are 2 or 3 groups, then there is also the option to rotate between groups on a daily basis in some embodiments. If there is no fractionation, only grouping, then the groups may be treated at least 1 day apart, but may be treated several days apart, for example once a week if desired.

In some embodiments the treatment plan generator includes a virtual dosimetry simulation (VDS) operation. A purpose of the VDS operation is to compare multiple grouping and fractionation solutions without having to call the dosimetry engine 192. Assessing 1-5 groups and 1-5 fractions over 1-15 allowable treatments would result in 21 different treatment sets, and a total of 57 groups. This cannot be compared manually, and would be difficult to run all of these solutions through a dosimetry engine 192. Therefore, in some embodiments the virtual dosimetry simulation operation is instead performed. In some embodiments, the VDS may also test "trivial grouping solutions" for comparison purposes, where all tumors have been placed into a single group, or where all groups contain a single tumor.

In some embodiments the VDS operation receives one or more inputs, such as the type of radiosurgical system, the list of tumor coordinates, volumes, and mean prescribed doses, a list of groups, details of normal structures, and an identification of each tumor that has been assigned to each group.

In some embodiments the output is the estimated dose to each normal dose point and tumor, and dose percentiles to the normal dose points (for example: D1, D5, D10, D20, D30, D50, D75, D90). D1 means that 1% of the normal dose points are receiving at least this many Gray of radiation. D10 means that 10% of the normal dose points are receiving at least this many Gray of radiation. D50 is the median dose to the NDPs. Doses to tumors are also listed by treatment group, including prescribed dose and median dose. In addition, in some embodiments the operation suggests reductions in prescription dose to each tumor to compensate for bystander dose contributions from the other groupings.

In some embodiments the VDS operation functions as a black box that mimics the actual dosimetry engine 192 as closely as possible.

One example of a VDS operation is performed as follows.

A set of normal dose points is created. The "brain" can be expressed as a box that is 2 cm beyond the outer diameter of all tumors, in all directions, or it can be expressed by the actual brain coordinates. Each tumor may be considered to be spherical or have detailed shape information. Normal dose points are placed every 1 cm within that box, but none are placed within a PTV.

The VDS operation cycles through every normal dose point and every tumor, and calculates the dose that is received at that point, by summating the radiation from every tumor placed into that group, according to (volume$^{2/3}$*1/distance$^{(2-ai)}$*dose), and incorporating other permissible beam direction information.

Next, there is an iterative modification to the radiation that each tumor emits, to compensate for the radiation that is being received from the other tumors within its group. The VDS operation cycles through again. This dose modification iteration is performed a few times until steady-state is reached.

The process is repeated for every group. The dosages are converted to BED values for each group. BED values are summated across groups for each normal dose point and for each tumor.

Next, some embodiments further include a second iterative process, wherein the prescribed dose to each tumor is adjusted to compensate for bystander dosage reaching it from outside its group. For example, dose contributions to a tumor from the other groups are compensated for.

In some embodiments the treatment plan generator 194 operates to perform a comparison of multiple different grouping assignments and to compare the results to each other, and to compare the results against a no-grouping assignment.

How is one set of normal dose points compared to another set in order to evaluate grouping solutions? Some points will be higher, some lower. In some embodiments the mean of the normal dose points can be used. In another embodiment, normal dose points that are receiving a low dose are not considered, and the mean is computed only from a specified percentage of the normal dose points that receive the largest radiation exposure, such as the top 50%.

Some embodiments utilize a Monte Carlo algorithm. Monte Carlo techniques involve using random numbers to test different solutions. With this method, a number of randomly chosen solutions (such as 5000) are chosen. For each randomly tested solution the number of groups is first randomly chosen based upon the minimum and maximum allowable. Tumors are then randomly assigned to different groups. If this is a unique sorting solution, then the VDS operation is run. If this produces the lowest summed BED for the matrix of normal tissue dose points for that particular number of groups, then this solution is retained as the best solution so far. When the VDS operation accurately approximates the actual planning, the Monte Carlo algorithm will produce effective groupings specifically tailored to a particular radiosurgery system.

An example output of the VDS operation is shown in Table 1, below.

TABLE 1

| Groups | Fract | D1 | D5 | D10 | D20 | D30 | D50 | D75 | D90 |
|---|---|---|---|---|---|---|---|---|---|
| 1 | 1 | | | | | | | | |
| 1 | 2 | | | | | | | | |
| 1 | 3 | | | | | | | | |
| 1 | 4 | | | | | | | | |
| 1 | 5 | | | | | | | | |
| 2 | 1 | | | | | | | | |
| 2 | 2 | | | | | | | | |
| 2 | 3 | | | | | | | | |
| 2 | 4 | | | | | | | | |
| 2 | 5 | | | | | | | | |
| 3 | 1 | | | | | | | | |
| 3 | 2 | | | | | | | | |
| 3 | 2 | | | | | | | | |

TABLE 1-continued

| Groups | Fract | D1 | D5 | D10 | D20 | D30 | D50 | D75 | D90 |
|---|---|---|---|---|---|---|---|---|---|
| 3 | 3 | | | | | | | | |
| 3 | 4 | | | | | | | | |
| 3 | 5 | | | | | | | | |
| ...G | ...F | | | | | | | | |

Using the output, the treatment plan generator can suggest the most efficient choice based on this data.

In some embodiments the treatment plan generator operates to evaluate and suggest potential modifications to the prescribed dose to achieve an intended dose. One example of such an output is shown in Table 2, below.

TABLE 2

This table is based upon 2 groups and 5 fractions, for a total of 10 treatments.

| Tumor | Prescribed dose | Median dose if no grouping | Median dose with grouping | Recommended adjustment of prescribed dose |
|---|---|---|---|---|
| PTV1 | 20 x 1 | 24.5 Gy x 1 | 28.3 Gy x 1 | 17.5 Gy x 1 |
| PTV2 | | | | |
| PTV3 | | | | |
| PTV4 | | | | |
| PTV5 | | | | |
| PTV6 | | | | |
| ... PTVn | | | | |

In some embodiments the treatment plan generator 194 prompts the medical professional to select whether to: (1) use original prescribed dosages, (2) use recommended adjustments of dosages, or (3) manually enter new dosages for each PTV.

Some embodiments consider the biologically effective dose. The biologically effective dose (BED) will now be discussed in further detail below.

A course of radiation therapy can be divided up into several smaller dosages, which are called "fractions." These fractions are spread over time and may be administered once every weekday over several days or weeks, for example. One purpose of fractionation is to help spare healthy surrounding tissues that are in the beam paths. The biologic effect of the daily radiation fraction size on tumors and on normal tissue is not simply a linear relationship; rather it is an exponential relationship. If you double the fraction size of radiation to a region of healthy brain tissue you may increase the damage by up to 3 to 4 times. If you divide a total radiation dose into 2 fractions that are given on two separate days, you will reduce the damage to normal tissue while maintaining the same summed total dose. The prediction of damage follows the linear quadratic model for estimating biologically effective dosages (BED) from radiation therapy.

Following a radiation treatment, there are tissues that respond early to radiation, and tissues that respond late. Early responding tissues include mucosal linings, skin, bone marrow, testis, and many tumors. Late responding tissues include brain, spinal cord, liver, and lung. Fractionation especially reduces the damage to late-responding tissues. A major reason why radiation therapy is traditionally fractionated over several weeks is to allow late-responding tissues such as the brain a chance to repair sub-lethal radiation damage. Unfortunately fractionation also reduces the BED to acute reacting tissues such as metastases, although to a lesser degree. Treating a tumor with 20 Gy×1 treatment is about 50% more powerful than treating with 10 Gy×2 treatments. Treating normal brain tissue with 20 Gy×1 treatment is about 83% more damaging than treating with 10 Gy×2 treatments.

The linear quadratic formula is BED=n*d*(1+d/(α/β)), described by Fowler, where BED=biologically effective dose, n=number of radiation fractions, d=radiation dose per fraction, and α/β is experimentally determined and is an indicator of how quickly a tissue responds to radiation. α/β is considered to be approximately 2.0 for normal brain tissue, and 10.0 for early responding tissues such as for some metastases. The physician may choose different values.

Table 1 illustrates an example of biologically effective dosages (BED) in tumor and normal brain for various fraction sizes of radiation therapy.

TABLE 3

| Daily radiation dose | Tumor Effect (BED) α/β = 10 | Normal Brain Effect (BED) α/β = 2 |
| --- | --- | --- |
| 1 Gy | 1.1 | 1.5 |
| 2 Gy | 2.4 | 4.0 |
| 3.33 Gy | 4.4 | 8.9 |
| 5 Gy | 7.5 | 17.5 |
| 10 Gy | 20.0 | 60.0 |
| 15 Gy | 37.5 | 127.5 |
| 20 Gy | 60.0 | 220.0 |

Some embodiments include a method of generating the treatment plan 280. One example is a method of generating a treatment plan for a radiosurgery device, the method comprising: assigning each of the tumors to one of a plurality of treatment groups, wherein a quantity of treatment groups is less than a quantity of the tumors; and generating a treatment plan including a treatment schedule for irradiating the tumors using the radiosurgery device in multiple treatment sessions based on the assigned treatment groups, wherein tumors assigned to different treatment groups are scheduled to be treated during different treatment sessions. In some embodiments the assigning is performed by a computing device as described herein. In some embodiments the generating of the treatment plan is performed by a computing device as described herein. In some embodiments the method is performed by one or more computing devices. Additionally, the various operations disclosed herein for the methods of treating multiple tumors using radiosurgery can also be performed for the method of generating a treatment plan for a radiosurgery device.

Some embodiments include a method of generating a treatment schedule for radiosurgery, the method comprising: assigning each of the tumors to one of a plurality of treatment groups using a computing device, wherein a quantity of treatment groups is less than a quantity of the tumors; and generating a treatment schedule including multiple treatment sessions using the computing device, wherein the tumors assigned to different treatment groups are treated in different treatment sessions.

Figure 12:
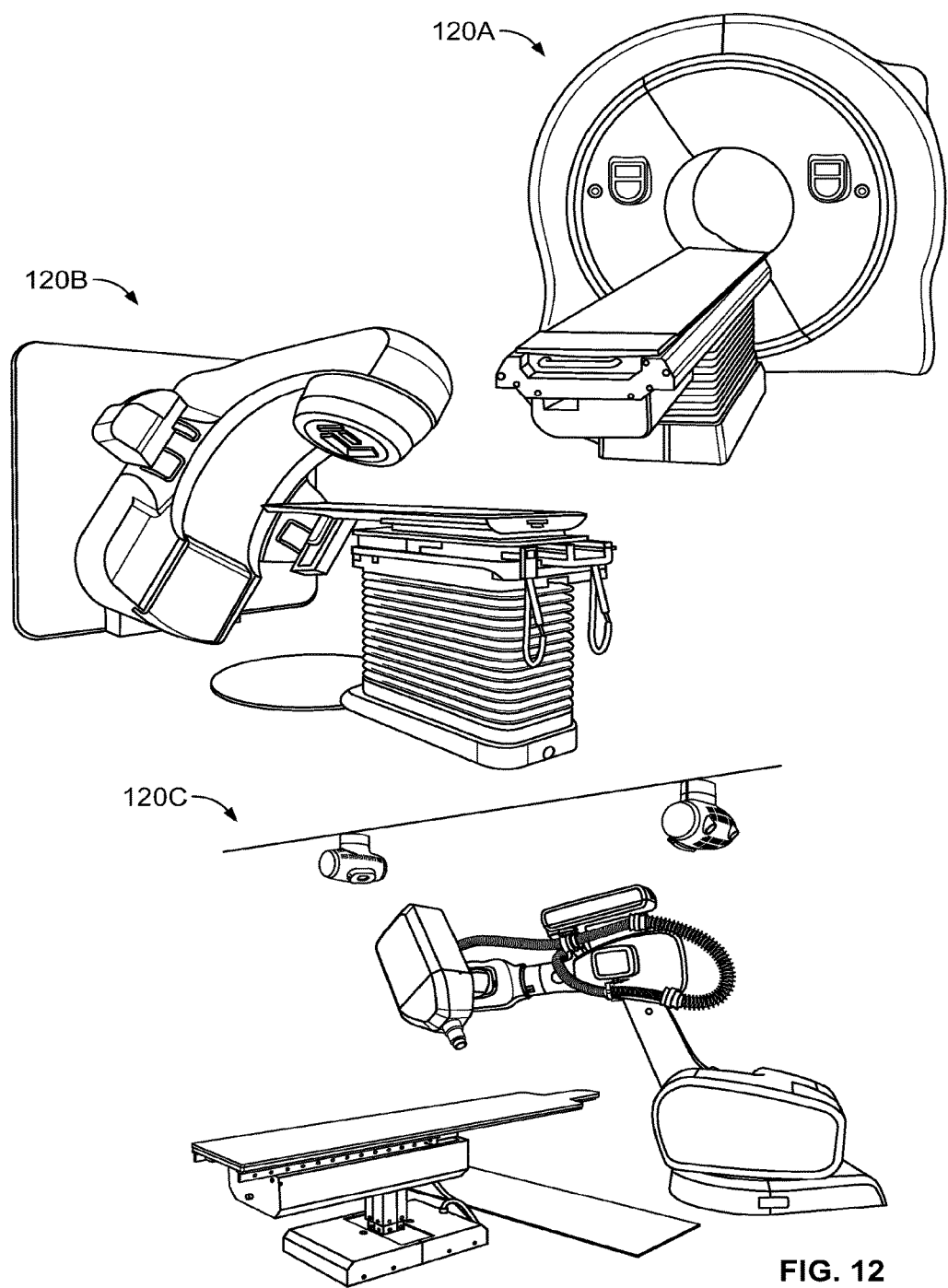
FIG. 12 illustrates several examples of the radiosurgery system shown in FIG. 1.

FIG. 12 illustrates several examples of the radiosurgery system 106, and more specifically examples of the radiosurgery device 120 (including 120A-C).

One example of a radiosurgery device 120A is the TomoTherapy brand treatment system available from Accuray Incorporated, of Sunnyvale, Calif.

Another example of a radiosurgery device 120B is the TrueBeam® brand radiotherapy system, available from Varian Medical Systems, of Palo Alto, Calif.

A further example of a radiosurgery device 120C is the CyberKnife brand robotic radiosurgery system, also available from Accuray Incorporated.

Other embodiments include other radiosurgery systems and devices. For example, another embodiment includes the Gamma Knife brand radiosurgery device available from Elekta AB of Stockholm, Sweden.

Following are several hypothetical examples that illustrate aspects of the present disclosure.

In this example, consider a patient having nine metastases in the brain, which range from 1 to 2.5 cm and some are in close proximity to one another. The patient strongly desires stereotactic radiosurgery and wants to avoid whole brain irradiation.

Scenario 1: All 9 tumors are treated together on the same day, 20 Gy×1. There appears to be a fairly large volume of normal tissue in between tumors that is receiving approximately 50% of the prescribed dose, i.e. 10 Gy. BED tumor=60 Gy, and BED brain (the 10 Gy or 50% region)=60 Gy. Therapeutic ratio=60/60=1.00.

Scenario 2: Temporal fractionation is used. In this example, the dose is increased to 10 Gy×3 fractions=30 Gy total to obtain the same anti-tumor effect. The area of normal brain tissue still receives 50% of the prescribed dose, i.e. 5 Gy×3 fractions. BED tumor=60 Gy, and BED brain=52.5 Gy. Therapeutic ratio=60/52.5=1.14.

Scenario 3: Grouping is used. The tumors are divided into 3 groups of 3 tumors each. Each group is treated on a separate day to a dose of 20 Gy×1. The large volume of normal brain tissue in between tumors now receives about ⅓ of 50% of the prescribed dose each day, i.e. a total of 3.3 Gy×3 fractions. BED tumor=60 Gy. BED brain=26.7 Gy. Therapeutic ratio=60/26.7=2.25.

This is an idealized example, but it demonstrates that grouping (also referred to as spatial grouping fractionation, or just spatial fractionation) has the ability to more powerfully spare normal brain tissue than does standard temporal fractionation. In reality there are zones of normal brain that will receive anywhere from 0 to 110% of the prescribed dose. Dividing up into treatment groups will create a very complex pattern of daily dose reductions throughout the brain. In addition, temporal fractionation may also be combined with spatial grouping fractionation in other embodiments to provide an even more powerful normal tissue sparing effect.

EXAMPLES

The following section discusses an example of an experimental result obtained based on one embodiment according to the present disclosure.

These are the results from the first dosimetric assessment that was performed. A pre-existing simulation CT scan and MRI scan were used to generate a dosimetric analysis. The patient was not actually treated with these grouping plans. The patient had 8 brain metastases that were all small. The tumors were all contoured and 20 normal dose points (NDP) were placed at strategic points within the brain. It was decided that 2 groups would be used. The tumor coordinates and volumes were entered into the grouping software, and the tumors were divided into 2 groups by using a grouping algorithm. On the TomoTherapy planning system we calculated 3 plans, for 20 Gy×1 for all eight tumors together, 20 Gy×1 for the first group of 4 tumors, and 20 Gy×1 for the second group. The resultant median tumor dosages and mean NDP doses were then converted to BED values for all 3 plans. The BED values from the group plans were summated together. Next, the dose values were scaled from 20 Gy×1 down to 13 Gy×2, 7 Gy×5, and 4 Gy×10, and were converted to BED values.

| Dose/Frac/Groups | PRE-SCRIBED BED TUMOR | ACTUAL BED TUMOR | BED NORMAL BRAIN | Therapeutic Ratio |
|---|---|---|---|---|
| 20 Gy, 1 frac, 1 group | 60.00 | 70.62 | 70.52 | 1.001 |
| 20 Gy, 1 frac, 2 groups | 60.00 | 82.42 | 55.10 | 1.496 |
| 26 Gy, 2 frac, 1 group | 59.80 | 69.70 | 64.35 | 1.083 |
| 26 Gy, 2 frac, 2 groups | 59.80 | 81.77 | 51.75 | 1.580 |
| 35 Gy, 5 frac, 1 group | 59.50 | 68.33 | 55.08 | 1.241 |
| 35 Gy, 5 frac, 2 groups | 59.50 | 80.81 | 46.71 | 1.730 |
| 40 Gy, 10 frac, 1 group | 56.00 | 63.51 | 44.93 | 1.414 |
| 40 Gy, 10 frac, 2 groups | 56.00 | 75.63 | 40.27 | 1.878 |

There are some interesting observations from this data:

Grouping had a bigger effect than fractionation on improving the therapeutic ratio.

Grouping and fractionation benefits were additive.

By doing grouping, there will be additional passive dosage that the tumors receive during the treatment of groups that the tumor does not belong to, of about 17% when 2 groups are used. This may not be desired, and perhaps the prescribed dose should be lowered slightly.

To compensate for the effect of increased BED to tumors, we compared schemes with the therapeutic ratio which is BED Tumor/BED Normal.

The most efficient solution is a matter of physician judgment, but may have been 2 groups with 2 fractions each.

This result was obtained with TomoTherapy® planning. A different radiation delivery system such as CyberKnife® would produce a different degree of benefit.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A radiosurgery treatment system comprising:
   at least one processing device;
   at least one computer readable storage device, the at least one computer readable storage device storing data instructions that when executed by the at least one processing device cause the at least one processing device to:
      assign each of multiple tumors to one of multiple treatment groups, wherein a quantity of the treatment groups is less than a quantity of the tumors; and
      generate a treatment schedule including multiple treatment sessions, wherein any two of the tumors that are assigned to different ones of the treatment groups are treated in different ones of the treatment sessions; and
   a radiosurgical device that is operable to treat an area containing at least some of the tumors according to the treatment schedule.

2. The radiosurgery treatment system of claim 1, wherein the data instructions, when executed by the at least one processing device, further cause the at least one processing device to generate a treatment protocol for each of the multiple treatment sessions using contour data for at least some of the multiple tumors.

3. The radiosurgery treatment system of claim 2, wherein the generation of the treatment protocol for each of the multiple treatment sessions further involves dose fractionation.

4. The radiosurgery treatment system of claim 1, wherein the at least one computer readable storage device is an optical storage medium.

5. The radiosurgery treatment system of claim 1, wherein the data instructions, when executed by the at least one processing device, further cause the processing device to:
   evaluate a patient having the multiple tumors to determine whether the patient is a candidate for radiation therapy involving the assignment of the multiple tumors to the multiple treatment groups;
   identify locations of the multiple tumors in images of an area of interest;
   determine appropriate radiation beam characteristics for radiosurgery;
   and
   define billing information associated with the radiosurgery.

6. The radiosurgery treatment system of claim 1, wherein the different ones of the treatment sessions are on different days.

7. The radiosurgery treatment system of claim 1, wherein the quantity of the treatment groups is in a range from two to five.

8. The radiosurgery treatment system of claim 1, further comprising a scanning device configured to perform a scan of a region of a body including the tumors to generate scan images, wherein the data instructions, when executed by the at least one processing device, further cause the processing device to:
   determine boundaries of the tumors in the scan images;
   expand the boundaries by a safety margin to determine a planned target volume for each of the tumors; and
   determine a location and the planned target volume for each of the tumors, using the location and the planned target volume when assigning each of the tumors to one of the treatment groups.

9. The radiosurgery treatment system of claim 8, wherein the scanning device is a computed tomography scanning device.

10. The radiosurgery treatment system of claim 8, wherein using the location and the planned target volume when assigning each of the tumors to one of the treatment groups is achieved by placing each of the tumors that have a greater dose impact on each other into different ones of the treatment groups.

11. The radiosurgery treatment system of claim 8, wherein the location is a centroid coordinate.

12. The radiosurgery treatment system of claim 1, wherein the assignment of each of the multiple tumors to one of the multiple treatment groups is performed to minimize a biologically effective dose to healthy tissue in a region of a patient-containing the multiple tumors.

13. The radiosurgery treatment system of claim 1, wherein the data instructions, when executed by the at least one processing device, further cause the processing device to:
   determine a quantity of the treatment groups;
   assign a first subset of the tumors with a greater dose impact to separate ones of the treatment groups; and
   for each remaining tumor, assign the remaining tumors to the separate ones of the treatment groups in order of largest to smallest dose impact by:
      determining, for a next remaining tumor, which one of the treatment groups contains a subset of the tumors that would create a lowest dose impact to a normal tissue if the next remaining tumor were to be added, and assign the next remaining tumor to that one of the treatment groups.

14. The radiosurgery treatment system of claim 13, wherein the data instructions, when executed by the at least one processing device, cause the processing device to determine which one of the treatment groups contains a subset of the tumors that would receive a lowest amount of radiation based on a summed dose impact for the subset of the tumors on a normal tissue.

15. The radiosurgery treatment system of claim 1, wherein the radiosurgical device is a device that can perform stereotactic radiosurgery as one of its functions.

16. The radiosurgery treatment system of claim 15, wherein the radiosurgical device is selected from a proton beam device, a Gamma Knife device, a CyberKnife device, an arc therapy device, or a multiple static beam device.

\* \* \* \* \*